United States Patent [19]
Schaper

[11] 4,075,136
[45] Feb. 21, 1978

[54] FUNCTIONAL IONENE COMPOSITIONS AND THEIR USE

[75] Inventor: Raymond Joseph Schaper, Pittsburgh, Pa.

[73] Assignee: Calgon Corporation, Pittsburgh, Pa.

[21] Appl. No.: 676,777

[22] Filed: Apr. 14, 1976

Related U.S. Application Data

[63] Continuation-in-part of Ser. No. 436,419, Jan. 25, 1974, abandoned.

[51] Int. Cl.[2] .......... C07D 211/00
[52] U.S. Cl. .......... 260/2 R; 210/54; 252/390; 260/290 R; 260/326.5 FL; 260/465.9; 260/468 J; 260/468 R; 260/561 A; 260/561 K; 260/561 S; 428/511; 526/11.1
[58] Field of Search .......... 260/2 R, 561 A; 526/11.1

[56] References Cited

U.S. PATENT DOCUMENTS

| | | | |
|---|---|---|---|
| 2,048,620 | 8/1962 | Spivack | 260/471 |
| 3,875,111 | 4/1972 | Tsuba et al. | 260/2 R |

*Primary Examiner*—Harold D. Anderson
*Attorney, Agent, or Firm*—Rudolph J. Anderson, Jr.; Mario A. Monaco; Martin L. Katz

[57] ABSTRACT

Novel functional ionene polymer compositions have been prepared which have been found to be useful in a wide variety of applications, including, among others, as wet and dry strength additives, corrosion inhibitors, and electroconductive coatings, and which comprise recurring units of the formula:

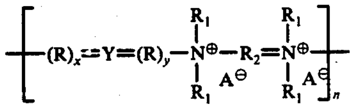

3 Claims, No Drawings

FUNCTIONAL IONENE COMPOSITIONS AND THEIR USE

This is a continuation-in-part of application Ser. No. 436,419, filed Jan. 25, 1974, now abandoned.

BACKGROUND OF THE INVENTION

This invention relates to novel functional ionene polymer compositions and their use. These compositions are derived from cationic polyelectrolyte structures based on ionic amine backbones. The compositions of this invention, however, additionally include various functional groups attached to this ionic amine backbone. Previously, developments in this area have been concerned with deriving novel structures solely for the benefit of the cationic nature of the resultant structure. Little attention has been paid to the make-up of the groups attached to the nitrogen atoms forming the backbone of the cationic polymer structure, and these groups have consequently been confined generally to simple alkyl groups. By contrast, the novel functional ionene polymer compositions of this invention have attached to the nitrogen atoms of the polymer backbone a number of different functional groups, the characteristics of which groups result in compositions useful in a variety of ways.

Useful applications of polymeric quaternary ammonium salts have long been known in the art. U.S. Pat. No. 2,261,002 discloses a number of uses for linear polymeric quaternary ammonium components of the formula:

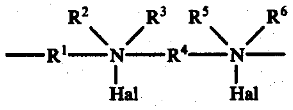

wherein Hal is a halogen of atomic weight at least 35; $R^1$ is an organic radical in which the atoms adjacent to nitrogen are carbon and are attached to other atoms only by single bonds; $R^2$, $R^3$, and $R^4$ are organic radicals attached to the nitrogen by carbon atoms and are so selected that not more than one of them is unsaturated; $R^5$ and $R^6$ are organic radicals attached to the nitrogen by carbon atoms and one of which may be unsaturated when $R^4$ is saturated; and $R^1$ and $R^4$ are different organic radicals attached to the nitrogen by carbon atoms and the sum of whose chain lengths exceeds five. The uses disclosed for the polymeric quaternary ammonium compounds include, among others, their use a photographic chemicals, pesticides, pour-point depressants, pigment dispersion control agents, and surface active agents.

U.S. Pat. No. 2,271,378 discloses compounds similar to those described in U.S. Pat. No. 2,261,002; and sets out their particular use as pest control agents.

U.S. Pat. No. 3,489,663 discloses electrolytic polymerization of ethylenically unsaturated monomers by applying an electric potential while the monomer is in a liquid diluent containing a polymeric ternary or quaternary onium compound as a conducting electrolyte. A preferred class of linear polymeric quaternary onium compounds useful in the patent method are those consisting essentially of recurring units represented by the formula:

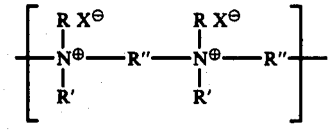

wherein R and R' each represent an alkyl (including cycloalkyl), aralkyl, aryl, or alkaryl radical. Another preferred class of quaternary onium compounds useful in the patent method are those consisting essentially of recurring units represented by the formula:

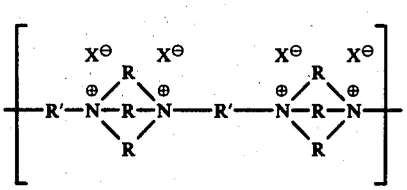

wherein R represents an alkylene or aralkylene radical.

U.S. Pat. No. 3,558,314 discloses light-sensitive silver halide material containing as a sensitizer a water soluble quaternary compound having the general formula:

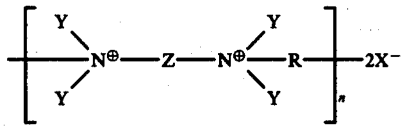

wherein Y is a radical selected from the group consisting of alkyl, phenylalkyl, hydroxyalkyl, alkoxyalkyl, acyloxyalkyl, aminoalkyl, alkylaminoalkyl, and acylaminoalkyl, the alkyl group of the radical having up to 18 carbon atoms.

U.S. Pat. No. 3,632,507 discloses a process for the flocculation of particles dispersed in aqueous media, which employs as a flocculant polymeric quaternary ammonium salts having repeating units of the general formula:

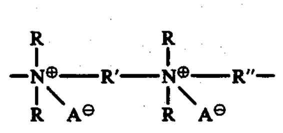

wherein R is a lower alkyl group, particularly an alkyl group containing 1–4 carbon atoms.

U.S. Pat. No. 3,632,559 discloses cationically active, water soluble polyamides obtained by alkylation with a bifunctional alkylation agent of the formula:

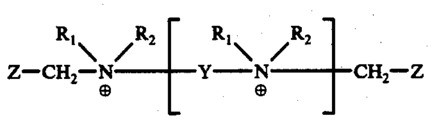

wherein each of $R_1$ and $R_2$ is selected from lower alkyl and lower hydroxy alkyl radicals.

U.S. Pat. No. 3,671,468 discloses polymers represented by the formula:

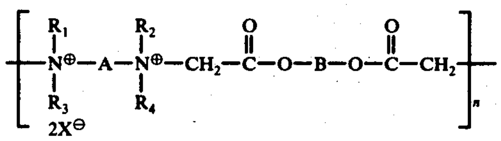

wherein $R_1$, $R_2$, $R_3$, and $R_4$ represent a lower alkyl group, or $R_1$ and $R_2$ and/or $R_3$ and $R_4$, when taken together with the nitrogen atoms to which they are attached, may form heterocyclic rings.

Canadian Pat. No. 878,585 discloses a process for preparing a water-soluble cationic polymeric polyelectrolyte which comprises reacting a particular class of dihalo organic compounds with a ditertiary amine in the presence of water. The resulting polymers are useful in a number of applications including utility as drainage aids, formation aids, retention aids, strength aids, and flocculants.

South African Pat. No. 71/5573 discloses a high molecular weight polymeric composition comprising a polymeric backbone to which is grafted an ionene type polymer by means of a coupling agent. A wide variety of uses for the compositions are described.

This invention is directed to novel functional ionene polymer compositions and to novel functional diamine intermediates useful in the preparation of the functional ionene polymer compositions.

The novel functional ionene polymer compositions of this invention may be represented by the formula:

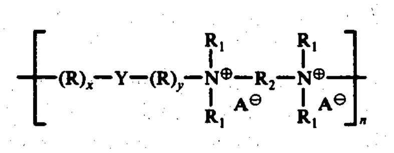

wherein R is independently selected from the group $CH_2$ and substituted $CH_2$ groups where one of the hydrogen atoms of the group is replaced by alkyl or hydroxymethyl;

wherein Y is a member selected from the group consisting of

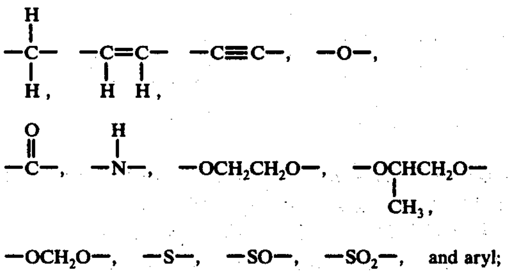

$—OCH_2O—$, $—S—$, $—SO—$, $—SO_2—$, and aryl;

wherein $R_1$ represents the group:

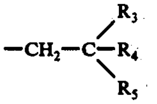

where $R_3$ is hydrogen, lower alkyl of from 1 to 4 carbon atoms, or lower alkenyl of from 1 to 4 carbon atoms; $R_4$ is hydrogen, halogen, straight or branched alkyl, cycloalkyl, aryl, alkaryl, or aralkyl; and where $R_5$ is a member selected from the group consisting of:

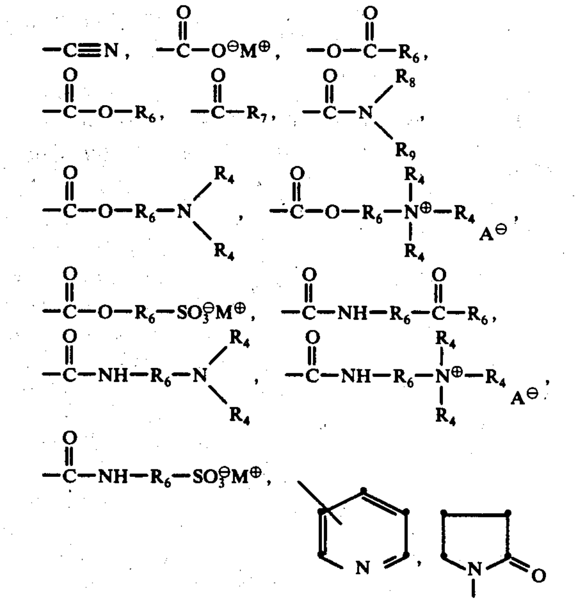

where $R_4$ has the same meaning as above;

wherein $R_6$ is selected from the group consisting of straight or branched alkyl, cycloalkyl, hydroxyalkyl and alkoxyalkyl;

where $R_7$ has the same meaning as $R_6$, additionally including hydrogen, haloalkyl and aryl;

where $R_8$ and $R_9$ are each independently selected from the group consisting of hydrogen, alkyl, hydroxyalkyl, cycloalkyl, aryl, alkaryl, aralkyl, and alkoxyalkyl;

where $M^+$ is hydrogen ion, alkali metal ion, alkaline earth metal ion, or ammonium;

wherein $R_2$ is a straight or branched alkyl chain of 1 to 18 carbon atoms, which may be interrupted by one or more atoms of oxygen or sulfur; aralkyl or cycloalkyl;

wherein $R^-$ is an anion; and wherein $x$ and $y$ are integers from 1 to 10; and $n$ is an integer of 2 or greater.

The functional ionene polymer compositions of this invention may be prepared, and have been found to be useful, in a wide range of molecular weights. The average molecular weight may be as low as about 300 or as high as 300,000 or more. Thus, $n$ may be an integer of 2 to 1000 or higher. The average molecular weight of the functional ionene polymer actually employed will be determined by the requirements of the particular use to which the polymer composition is being put.

SUMMARY OF THE INVENTION

It has been indicated that this invention relates to the preparation and use of novel functional ionene compositions. The term "aliphatic ionene" was first suggested by A. Rembaum and his co-workers [Polymer Letters, 6, 160, (1968)] as a generic name for ionic amines, and the term has since gained acceptance in the field of polyelectrolyte chemistry. The term "ionene" is thus used herein to denote polymers containing ionic amine groups, particularly quaternary ammonium groups.

The term "functional" is used herein to denote substituent groups appended to the nitrogen atoms of the quaternary ammonium polymer backbone, which are derived from chemical groups, that is, molecules characterized by recognized chemical activity, in a manner which will be later described herein.

Up to the present time, investigation and development in the area of ionenes has concerned itself with the building of ionene structures with the end view of providing novel cationic polymers, and utilizing that cationic structure for some proximate application which depends on the cationic function of the polymer. By contrast, it is an object of the present invention to provide novel ionene structures containing functional groups appended to the nitrogen atoms of the polymer backbone, thus giving rise to structures that have the potential of having properties over and above that possessed by the ordinary alkyl-type ionenes.

The novel functional ionene polymers of this invention are prepared in what is essentially a two-step process employing three basic chemical structure materials. This two-step process may be conveniently illustrated by the following flow diagram:

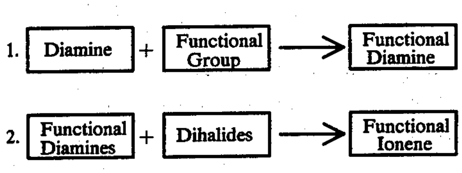

A simple example will serve to better illustrate this preparation method. In this example the basic diamine building block is ethylene diamine. This diamine is reacted with acrylamide by way of the Michael addition to give the following functional diamine:

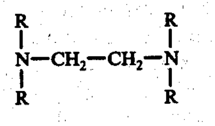

where R is $CH_2—CH_2—CONH_2$. It will be noted that the reaction is one of addition and that the diamine substituent or substituents are added across the double bond to the $\beta$ carbon atom of the functional group or groups. In this example the ethylene diamine has been completely reacted so as to produce a diamine fully substituted with propionamido groups. However, such complete substitution is not necessary, and this invention also contemplates lesser degrees of substitution, but does require the substitution of at least one functional group. The diamine fully substituted with propionamido group is next reacted with a dihalide, which in this example is bis-chloroethylether. A functional ionene with the following repeating unit results:

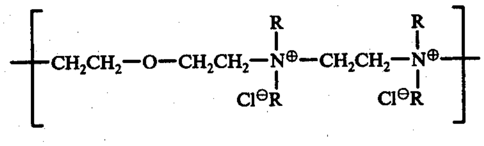

where R is $CH_2—CH_2—CONH_2$.

By utilizing more than one type of substituted functional diamine, a greatly increased number of different functional ionene structures is possible. For example, in addition to the tetrapropionamidoethylenediamine employed above, it is possible to additionally employ tetraallylethylenediamine in the reaction with bis-chloroethylether. The following functional ionene repeating unit results:

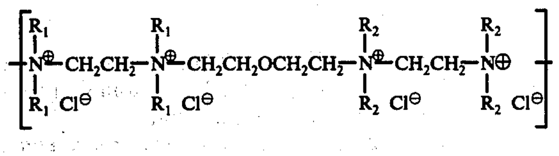

where $R_1$ is $CH_2CH_2CONH_2$ and $R_2$ is $CH_2CH{=}CH_2$.

It is also possible to prepare mixed functional diamines, and this invention contemplates the use of such mixed functional diamines in preparing the functional ionene compositions of this invention. For example, by the Michael addition with acrylamide to N,N-dimethylpropylenediamine the following mixed functional diamine may be prepared:

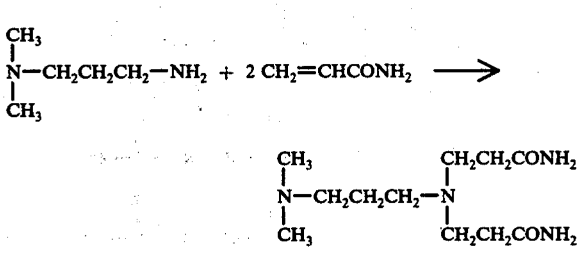

While a method has been described for preparing the functional ionene polymer compositions of this invention, it is evident that other methods also clearly recommend themselves for use in preparing the compositions of this invention. For example, use may be made of a starting material from which the functional ionene polymers of this invention may be prepared directly. Such a starting material would be, for example:

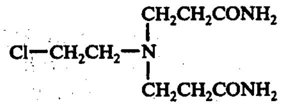

Diamines useful in preparing the functional ionene polymer compositions of this invention may be represented by the formula:

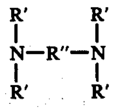

wherein at least one R' is H, although it is preferred that as many as two to all four of the R' groups be H. When R' is not H, it may be lower alkyl of from 1-4 carbon atoms or alkenyl of from 1-4 carbon atoms. R'' is a straight or branched alkylene group of 1-18 carbon atoms, wherein the carbon atom chain may be interrupted by one or more atoms of oxygen or sulfur. R'' may also be aralkyl, for example xylyl, or cycloalkyl, for example cyclohexyl. Compounds capable of introducing functional groups in preparing the functional ionene polymers of this invention may be represented by the formula:

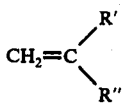

wherein R′ is hydrogen, halogen, straight or branched alkyl, cycloalkyl, aryl, alkaryl, aralkyl, heterocyclic and substituted heterocyclic; and wherein R″ is selected from the radicals represented by the following formulas:

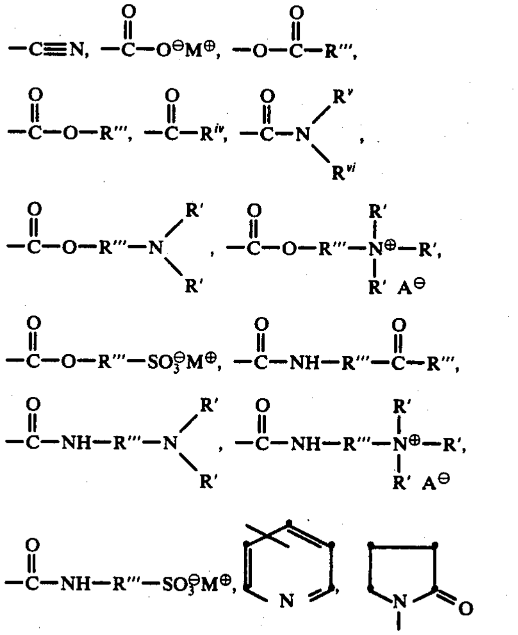

where R′ has the same meaning as above;

where R‴ is selected from the group consisting of straight or branched alkyl, cycloalkyl, hydroxyalkyl and alkoxyalkyl;

where $R^{iv}$ has the same meaning as R‴, additionally including hydrogen, haloalkyl and aryl;

where $R^{v}$ and $R^{vi}$ are each independently selected from the group consisting of hydrogen, alkyl, hydroxyalkyl, cycloalkyl, aryl, alkaryl, aralkyl, and alkoxyalkyl;

where $M^{+}$ is hydrogen ion, alkali metal ion, alkaline earth metal ion, or ammonium; and where $A^{-}$ is an anion.

The anions, designated herein as $A^{-}$, which usually constitiute the counterions for cationic quaternary ammonium groups, are of subordinate importance chemically. Thus, $A^{-}$ may be any anion, but is especially halide, alkylsulfate, e.g. methyl sulfate, tosylate, carboxylate, sulfonate, e.g. toluene sulfonate, sulfate, phosphate, acetate, nitrate, and so forth.

Dihalide compounds useful in preparing the funcrional ionene polymer compositions of this invention may be represented by the formula:

$$X—(R')_m—Y—(R')_n—X$$

wherein X is halogen, preferably Br or Cl;

wherein R′ is independently selected from a $CH_2$ group and substituted $CH_2$ groups where one of the hydrogen atoms of the group is replaced by alkyl or hydroxymethyl;

wherein *m* and *n* are integers of 1 to 10 and may be the same or different; and wherein Y is selected from the group consisting of aryl and radicals represented by the following formulas:

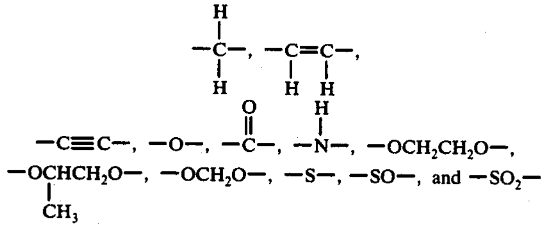

Examples of dihalide compounds which would be useful in preparing the functional inonene polymer compositions of this invention include, among others, bis-(chloromethyl)ether, bis(2-chloroethyl)ether, bis(2-chloropropyl)ether, bis(4-chlorobutyl)ether, oxy-3-bis-(2-chloropropanol-1), bis(2-chloroethyl)sulfide, bis(2-chloroethyl)sulfoxide, bis(2-chloroethyl)sulfone, bis-(3-chloropropyl)sulfide, bis(2-chloropropyl)sulfone, bis-(2-chloroethoxy)ethane, 1,2-bis(2-chloropropoxy)propane, 1,3-dichloropropanone-2, 1,3-dichloropropanol-2, bis(2-chloromethyl)amine, 1,4-bis(chloromethyl)benzene, 1,5-bis(chloromethyl)naphthalene, 9,10-bis(-chloromethyl)anthracene, chloroethyl-chloromethyl ether, 1-(4-chlorobutyl)chloromethyl ether, chloroethyl-chloromethyl sulfide, chloroethyl-chloromethylsulfoxide, and chloroethyl-chloromethyl sulfone.

Specific functional groups from which various specific functional ionene compositions of the present invention may be derived are summarized in the following table which designates the constituents of the general formula for the functional group and shows and names the resultant functional group. The R′ and R‴ through $R^{vi}$ substituents are defined as explained above for the same designations.

Functional Group General Formula:

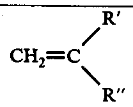

| Generic Group R′ | R‴ | Formula for R″ | Name and Structure of Resulting Functional Group |
|---|---|---|---|
| $CH_3$ | —C≡N | —C≡N | 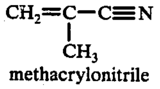 methacrylonitrile |

-continued
Functional Group General Formula:
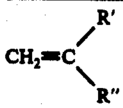
| Generic Group R' | of Resulting R''' | Formula for R'' | Name and Structure Functional Group |
|---|---|---|---|
| H | 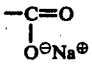 | 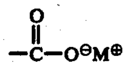 | 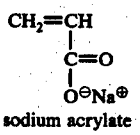 sodium acrylate |
| $CH_3$ | 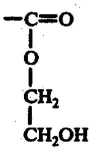 | 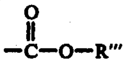 | 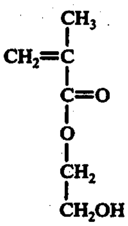 2-hydroxyethyl methacrylate |
| H | 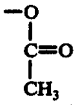 | 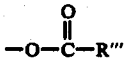 | 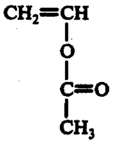 vinyl acetate |
| H | 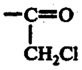 | 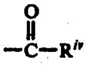 | 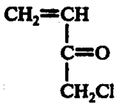 chloromethyl vinyl ketone |
| H | 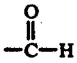 | 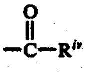 | 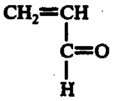 acrolein |
| H | 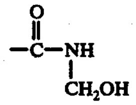 | 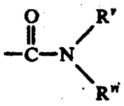 | 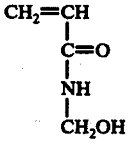 N-methylol acrylamide |
| H | 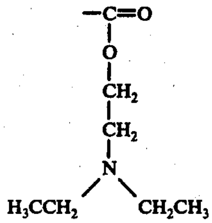 | 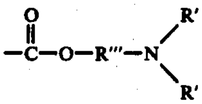 | 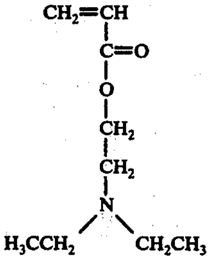 N,N-diethyl aminoethyl acrylate |

-continued
Functional Group General Formula:
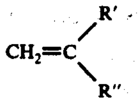
| Generic Group R' | R''' | Formula for R'' | Name and Structure of Resulting Functional Group |
|---|---|---|---|
| $CH_3$ | 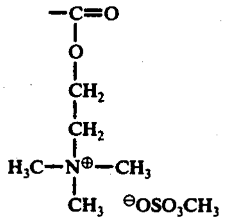 | 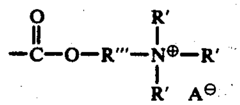 | 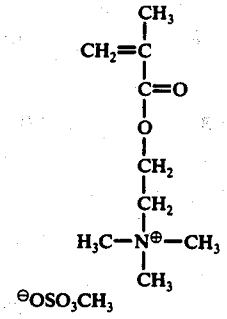 methacryloyloxyethyl trimethyl ammonium methosulfate |
| $CH_3$ | 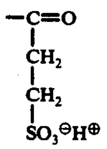 | 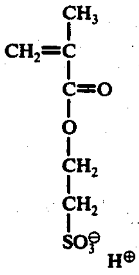 | 2-sulfoethyl methacrylate |
| H | 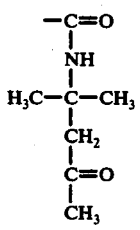 | 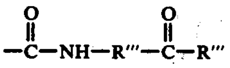 | 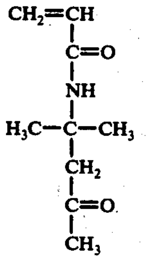 diacetone acrylamide |
| H | 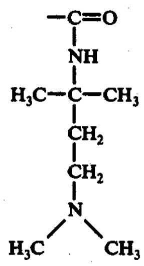 | 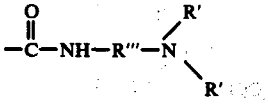 | |

-continued

Functional Group General Formula:

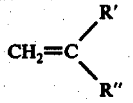

| Generic Group R' | R''' | Formula for R'' | Name and Structure of Resulting Functional Group |
|---|---|---|---|
| 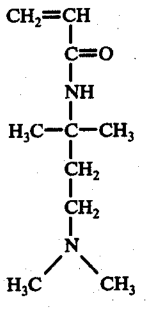 | | | acrylamidomethylbutyl dimethyl amine |
| $CH_3$ | 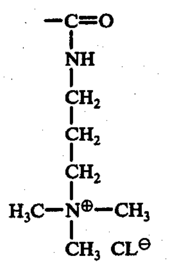 | 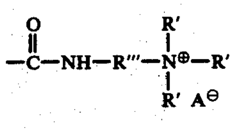 | 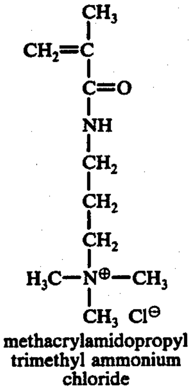 methacrylamidopropyl trimethyl ammonium chloride |
| H | 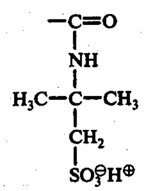 | 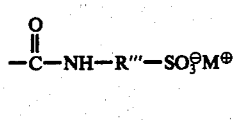 | 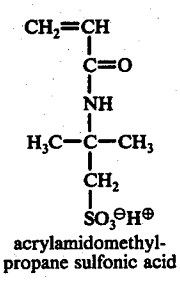 acrylamidomethyl-propane sulfonic acid |
| H | 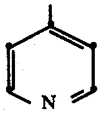 | 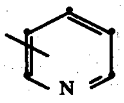 | 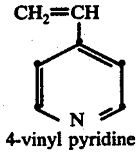 4-vinyl pyridine |
| H | 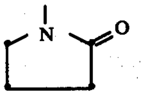 | 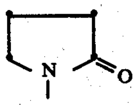 | 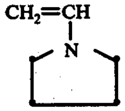 N-vinyl-2-pyrrolidone |

The novel functional ionene compositions of this invention have been found to be useful in a number of different application areas. The usefulness of these compositions for some particular purpose may variously depend upon the basic cationic nature of the polymer structure, or upon the chemical and physical properties of the functional group or groups employed in preparing the functional ionene polymer compositions as previously described, or upon both.

The functional ionenes of this invention are useful in four broad areas of application: (1) as processing aids; (2) as significant process modifiers; (3) as valuable additions to a given product; and (4) as products themselves.

As processing aids, the functional ionenes of this invention may be employed as solids/liquid separation aids, particularly as coagulants and flocculants. They may be employed as dewatering aids for sewage and mineral sludges. They are useful as flotation aids and as scale and deposit inhibitors. In the paper industry they find use as pigment retention aids, as drainage aids, and as sheet formation aids. The functional ionenes of this invention are also useful as chelating agents, demulsifiers catalysts and biocides.

As significant process modifiers, the functional ionenes of this invention may be employed to modify the rheological properties of fluids. They may be used, for example, as friction reducers or turbulence suppressors, as mobility control agents in oilfield flooding for secondary recovery, and as gelling agents. The functional ionenes may be employed as dispersants for pigments, clays, sludge and other materials in both water and oil-based systems.

As valuable additional components of given products, the functional ionenes of this invention may be employed as wet and dry strength resins in paper, and as functional coatings on paper, for example, electroconductive, adhesive and photosensitive coatings. They may be used as components of various consumer products, for example, shampoos, antistatics, and cosmetics, among others. They may be used as textile finishing products for soil release, antistatic and other uses. They may be used as detergents and as detergent additives to, for example, lubricating oils.

As products themselves, the functional ionenes of this invention may be permeable membranes for use, for example, in electrodialysis. They may be used in biomedical applications as for example, non-thrombogenic materials. They may be used as gels or films for cosmetic purposes. They may be coatings produced by electrodeposition. They may be used as ion exchange or metal chelating reins, and as polysalt complexes. They may be used as modified plastics or as modified fibers.

Other specific uses for the functional ionenes of this invention which may be conveniently placed under one of the broad areas of application discussed above, are, as flame retardants, hair sprays, sequestering agents, grease thickening agents, dye mordants and dyeable assists in fibers and photographic film, emulsion stabilizers and emulsifiers, corrosion inhibitors, softening agents for fabrics and paper, silver halide peptizers and sensitizers for photographic film, agents for the isolation of proteins, printink inks and adhesives.

This invention will be further described by way of the following examples which illustrate both the preparation of representative functional ionene polymer compositions of this invention, as well as the utilization of the compositions of this invention in the various indicated areas. These examples are, however, merely illustrative and are not intended to in any way limit the scope of this invention.

EXAMPLE 1

Preparation of N,N,N',N'-Tetrapropionamide-ethylenediamine (TPEDA)

The following materials and amounts were employed in the preparation:

| | Amount (Grams) | Mol. Wt. | Moles |
|---|---|---|---|
| Ethylenediamine | 192 | 60 | 3.2 |
| Acrylamide | 896 | 71 | 12.6 |
| Water | 896 | — | — |

The acrylamide monomer and magnetic stirring bar were charged to a 3 liter resin kettle, which was fitted with a condenser, thermometer, and dropping funnel. The water was then added and the acrylamide monomer dissolved therein. The ethylenediamine was charged into the dropping funnel. When dissolving of the acrylamide monomer was completed, the temperature of the solution was raised to 20° C. The ethylenediamine was then added aver a 45 minute period, during which addition the temperature was maintained between about 20° and about 33° C. by cooling. After addition of the ethylenediamine was complete, the cooling bath was removed, and the temperature of the reaction mixture was permitted to rise unimpeded. The temperature of the reaction mixture was observed to peak at about 38° C. after 15 minutes time. The reaction mixture, which at that point was a deep gold, slightly viscous solution, was stirred overnight without external heating or cooling. The following day, the resin kettle was solid with a white precipitate, which was filtered off, washed with acetone, and vacuum-dried in a heated dessicator overnight at 40° C. under a vacuum of 20 mm. of Hg. The total yield was 933.8 g., or 84% based on ethylenediamine. Theoretical yield of N,N,N',N'-tetrapropionamide-ethylenediamine (TPEDA) would be 1101 g. Product structure was consistent with NMR analysis. Other characterization analyses were undertaken on the reaction product. Parts-by-weight percentages for the atomic constituents of the reaction product were calculated and then determined by analysis, giving the following results:

| For $C_{14}H_{28}O_4N_6$ | C | H | N |
|---|---|---|---|
| Calculated | 48.70 | 8.14 | 24.4 |
| Found | 48.47 | 8.29 | 23.4 |

A test for secondary amine using $NiCl_2/Cl_2/CS_2$ gave negative results. Titration indicated two inflection points due to two amine functions. The moisture content was found to be less than 1% by weight. The reaction product was found to be soluble in water with heating, and insoluble in methanol, DMF, acetone and ethanol.

EXAMPLE 2

Preparation of N,N,N',N'-tetra[3-acrylamido-3-methylbutyl trimethyl ammonium chloride]ethylenediamine (TAMBTACEDA) N,N,N'

The following materials and amounts were employed in the preparation:

| | Amount (Grams) | Mol. Wt. | Moles |
|---|---|---|---|
| Ethylenediamine | 6 | 60 | 0.1 |
| AMBTAC* | 94 | 235 | 0.4 |
| Water | 94 | — | — |

*AMBTAC is 3-acrylamido-3-methylbutyl trimethyl ammonium chloride.

The AMBTAC monomer, water and a magnetic stirring bar were charged into a 500 ml. flask fitted with thermometer, condenser and dropping funnel. The ethylenediamine was charged into the dropping funnel. After the AMBTAC monomer was dissolved, the ethylenediamine was added dropwise over a 2 minute period. During this time the temperature rose from 25° to 29° C. After the addition of ethylenediamine was complete, the reaction mixture was heated to 40° C. and held at that temperature for two hours. No precipitate formed and the reaction mixture was brought to a 75% concentration by removing a portion of the water with benzene. Acetone was then added to the reaction mixture and hygroscopic white precipitate was formed. The precipitate was dried under vacuum, which resulted in a glassy material, and this material was utilized without further treatment.

Product characterization using NMR analysis was consistent with the proposed structure.

EXAMPLE 3

Preparation of N,N'-dimethyl-N,N'-dipropionamido-ethylenediamine (DMDPEDA)

The following materials and amounts were employed in the preparation:

| | Amount (Grams) | Mol. Wt. | Moles |
|---|---|---|---|
| N,N'-dimethylethylenediamine (DMEDA) | 88 | 88 | 1.0 |
| Arylamide | 142 | 71 | 2.0 |
| Water | 142 | — | — |

The acrylamide monomer and a magnetic stirring bar were charged into a 500 ml. 3-neck flask fitted with thermometer, condenser and dropping funnel. The water was then added and stirring initiated to solubilize the acrylamide monomer. The N,N'-dimethylethylenediamine (DMEDA) was then charged into the dropping funnel after the acrylamide monomer was dissolved the DMEDA was added over a 45 minute period, with the temperature being maintained within 30° and 35° C. with cooling. After the addition was completed, the cooling bath was removed and the temperature allowed to rise to 36° C. The reaction mixture was stirred overnight without external heating or cooling. The following day, the reaction flask was found to be solid with a white precipitate, which was filtered off and washed with acetone. The white precipitate was vacuum-dried in a heated dessicator overnight to yield 134.5 grams, which represents a 59.5% yield based on DMEDA.

Product characterization using NMR analysis was consistent with the proposed structure. Other characterization analyses were undertaken on the reaction product. Parts-by-weight percentages for the atomic consstituents of the reaction product were calculated and determined by analysis, giving the following results:

| For $C_{10}H_{22}O_2N_4$ | C | H | N |
|---|---|---|---|
| Calculated | 52.2 | 9.57 | 24.3 |
| Found | 50.4 | 9.89 | 24.1 |

The melting point for the reaction product was determined to be 120° C.

EXAMPLE 4

Functional ionene reaction product of N,N,N',N'-tetrapropionamido-ethylenediamine (TPEDA) and 1,4-dibromobutane (DBB)

The following materials and amounts were used in the preparation:

| | Amount (Grams) | Mol. Wt. | Moles |
|---|---|---|---|
| TPEDA | 17.2 | 344 | 0.05 |
| DBB | 10.8 | 216 | 0.05 |
| Water | 28.0 | — | — |

the TPEDA and a magnetic stirring bar were charged into a 100 ml. 3-neck flask fitted with thermometer, condenser and dropping funnel. Once the TPEDA was dissolved the DBB was added, and the reaction mixture was then heated to reflux (95°–100° C.) and held at that temperature for 136 hours. For the purpose of analytical procedures, a white solid was recovered from the aqueous solution by pouring the solution into acetone.

Product characterization by means of NMR analysis confirmed the expected structure. Other characterization analyses were performed. Parts-by-weight percentages for the atomic constituents of the reaction product were calculated and determined by analysis giving the following results:

| For $C_{18}H_{36}O_4N_6Br_2$ | C | H | N |
|---|---|---|---|
| Calculated | 38.6 | 6.44 | 15.0 |
| Found | 41.3 | 6.67 | 14.6 |

The moisture content of the reaction product was determined to be 8.2% by weight.

EXAMPLE 5

Functional ionene reaction product of N,N'-dimethyl-N,N'-dipropionamide-ethylenediamine (DMDPEDA) and 1,4-dibromobutane (DBB)

The following materials and amounts were used in the preparation:

| | Amount (Grams) | Mol. Wt. | Moles |
|---|---|---|---|
| DMDPEDA | 100 | 230 | 0.435 |
| DBB | 94 | 216 | 0.435 |
| Water | 194 | — | — |

The DMDPEDA, DBB and water were charged into a 500 ml. flask fitted with a thermometer and condenser. Stirring was accomplished with a magnetic stirring bar. The solution of the ingredients was heated to reflux (95°–100° C.) and maintained for five days. Subsequent to heating the solution was concentrated and poured into methanol, from which a white precipitate was recovered.

Product characterization using NMR analysis gave the expected structure. Additional characterization analyses were undertaken on the functional ionene reaction product. Parts-by-weight percentages for the atomic constituents of the reaction product were calculated and determined by analysis, giving the following results:

| For $C_{14}H_{30}N_4O_2Br_2$ | C | H | N |
|---|---|---|---|
| Calculated | 37.7 | 6.72 | 12.6 |
| Found | 41.6 | 6.86 | 11.5 |

Moisture content of the reaction product was observed to be 9.0% by weight. Onset of decomposition for the reaction product was observed to be 117° C.

EXAMPLE 6

Functional ionene reaction product of N,N,N',N'-tetra-(3-acrylamido-3-methylbutyl trimethyl ammonium chloride) ethylenediamine (TAMBTACEDA) and 1,4-dibromobutane (DBB)

The following materials and amounts were used in the preparation:

| | Amount (Grams) | Mol. Wt. | Moles |
|---|---|---|---|
| TAMBTACEDA | 25 | 1000 | 0.025 |
| DBB | 5.4 | 216 | 0.025 |
| Water | 22.1 | — | — |

The TAMBTACEDA, DBB and water were combined in a 100 ml. 1-neck flask. The reaction mixture was heated at reflux (95°-100° C.) for five days. After the heating was complete, the solution was concentrated on a rotary evaporator and a solid was precipitated by the addition of acetone. NMR analysis confirmed the expected structure. Additional characterization analyses on the reaction product was undertaken. Parts-by-weight percentages for the atomic constituents of the reaction product were calculated and determined by analysis, giving the following results:

| For $C_{50}H_{108}N_{10}O_4Cl_4Br_2$ | C | H | N |
|---|---|---|---|
| Calculated | 49.4 | 8.91 | 11.5 |
| Found | 42.6 | 9.01 | 10.5 |

The moisture content of the reaction product was determined to be 14.6% by weight.

EXAMPLE 7

Electroconductivity

In this method the electroconductivity of the functional ionene polymer compositions was tested as resistance to the flow of an electrical current by the compositions when coated on a flat substrate. In this example paper was used as such a substrate.

A solution of the polymer composition to be tested was prepared and formed onto a paper substrate suitable for applying elctroconductive coatings (such as Bergstrom's copy paper base stock 20 lb./ream: 3000 ft.$^2$) by means of a Mayer wire-wound draw rod. The variations in the coating thicknesses were obtained with changes in the size of the draw rod used. The coated paper was dried to the touch in an oven maintained at 105° C. After drying, the paper was conditioned in a constant conditions room for at least 16 hours, after which the conditioned paper was placed in a chamber maintained at a relative humidity of 13%, where the paper was conditioned for at least 24 hours. The coated paper (3.175 inches wide cut and measured) was then passed through a Keithly Resistivity Adapter, with the coated side down, where a voltage of 100 volts was applied. The electrical current passing through the surface of the coated paper substrate was read using a Keithly Electrometer. The electrical current was read in amperes, and the surface resistivity was calculated from the following equation:

$$\text{Surface resistivity (ohms)} = 53.4 \times V/A$$

$V$ = Applied voltage $A$ = Electrometer reading - in amperes

The results of the test for electroconductivity are summarized in the table below:

| Composition | Coat Weight lbs./3000 ft.$^2$ | Surface Resistivity At 13% R.H. |
|---|---|---|
| TPDEA/DBB[1] | 1.6 | $>10^{15}$ |
| " | 0.95 | $>10^{15}$ |
| " | 0.79 | $>10^{15}$ |
| " | 0.48 | $>10^{15}$ |
| " | 0.16 | $>10^{15}$ |
| DMDPEDA/DBB[2] | 1.6 | $4.45 \times 10^{15}$ |
| " | 1.3 | $5.34 \times 10^{15}$ |
| " | 0.95 | $>10^{15}$ |
| " | 0.64 | $>10^{15}$ |
| " | 0.16 | $>10^{15}$ |
| TAMBTACEDA/DBB[3] | 1.4 | $8.34 \times 10^{15}$ |
| " | 1.1 | $1.07 \times 10^{15}$ |
| " | 0.95 | $1.41 \times 10^{15}$ |
| " | 0.64 | $1.98 \times 10^{15}$ |
| " | 0.48 | $3.56 \times 10^{15}$ |
| " | 0.16 | $>10^{15}$ |

[1]TPEDA/DBB = The functional ionene reaction product of Example 4.
[2]DMDPEDA/DBB = The functional ionene reaction product of Example 5.
[3]TAMBTACEDA/DBB = The functional ionene reaction product of Example 6.

EXAMPLE 8

Dry Strength

The functional ionene polymer compositions were evaluated for dry strength enhancing properties by preparing a series of hand sheets on a Noble Wood hand sheet forming machine, using the various polymer composition additives. The hand sheets were conditioned at 50% relative humidity at 70° F. for a minimum of 24 hours. The hand sheets were then tested for burst and tensile strength, with the values for these reported as a percentage increase over the blank. The blank hand sheets were prepared under the same conditions, except that no polymer dry strength additive compositions were employed.

The pulp stock used in preparing the hand sheets was bleached, hardwood sulfite pulp. The freeness was 650 ml. Schopper Reigler. Two percent alum was added. The dry strength polymer compounds were added to the headbox and mixed there for 3 minutes. The preparation was done in acid and alkaline media, with the headbox and sheet mold pH's being adjusted to 4.5 and 8.6 with 0.5 $NH_2SO_4$. There was no white water circulation during the preparation. The sheets were dried for 5 minutes at 230° F. before conditioning and evaluating. The burst strength was tested by a Mullen Tester according to TAPPI standard test procedure T403. The tensile strength was tested by a TMI instrument in accordance with TAPPI standard test procedure T404.

The results for the dry strength testing procedure are summarized in the following table.

| Composition | Feed-rate lbs./ton | Dry Tensile | % Over Blank | Burst | % Over Blank |
|---|---|---|---|---|---|
| | pH = 4.5 | | | | |
| | — | 6.7 | — | 9.2 | — |
| TPEDA/DBB | 20 | 6.9 | 3 | 10.2 | 10 |
| DMDPEDA/DBB | 20 | 7.1 | 6 | 12.0 | 30 |

-continued

| Composition | Feed-rate lbs./ton | Dry Tensile | % Over Blank | Burst | % Over Blank |
|---|---|---|---|---|---|
| TAMBTACEDA/DBB | 20 | 6.7 | — | 11.0 | 20 |
| | pH = 8.6 | | | | |
| | — | 6.3 | — | 12.0 | — |
| TPEDA/DBB | 20 | 6.5 | 3 | 11.7 | −2.5 |
| DMDPEDA/DBB | 20 | 6.8 | 8 | 12.5 | 4 |
| TAMBTACEDA/DBB | 20 | 6.9 | 10 | 13.5 | 12.5 |

EXAMPLE 9

Wet Strength

The wet strength enhancing properties of the ionene polymer compositions were evaluated in a manner similar to that described in Example 9. A 50/50 bleached, soft wood and hard wood Kraft pulp was beaten to a Schopper Reigler freeness of 750 ml. Portions of the pulp were mixed with the wet strength additive compositions at the percentage feed rate shown in the table below (based on pulp solids). The mixing was accomplished by means of a Heller stirrer for one minute, then transferred to the proportioner of a Noble Wood hand sheet forming machine. The pulp was formed into hand sheets of about 30 lbs. per 3,000 ft.$^2$ basis weight, dried 5 minutes at 232° F., then cured at 105° C. for 2 hours. A blank hand sheet was prepared in the same manner, except no wet strength additive was employed. The hand sheets were conditioned at 72° F. and 50% relative humidity for at least 24 hours. The sheets were tested on a TMI instrument for dry tensile strength as well as wet tensile strength after a 10 minute soaking in distilled water. The ratio of wet tensile strength to dry tensile strength expressed as a percentage equals percent wet strength.

The results for the testing procedure just described are summarized in the table below.

| Composition | 0.5% Feedrate | 1.0% Feedrate | 2.0% Feedrate |
|---|---|---|---|
| | % Wet Strength, pH = 4.5 | | |
| Blank | 7.3 | — | — |
| TPEDA/DBB | 7.4 | 7.4 | 6.2 |
| " | 7.1 | 8.0 | 8.4 |
| " | 6.3 | 6.2 | 5.8 |
| " | 8.0 | 8.4 | 8.8 |
| " | 8.1 | 8.0 | 9.4 |
| DMDPEDA/DBB | 7.4 | 6.0 | 7.4 |
| " | 7.1 | 8.9 | 9.1 |
| " | 7.2 | 8.8 | 10.7 |
| " | 7.6 | 9.0 | 9.7 |
| TAMBTACEDA/DBB | 6.3 | 6.6 | 7.6 |
| | % Wet Strength, pH = 7.5 | | |
| Blank | 8.6 | — | — |
| TPEDA/DBB | 7.5 | 7.8 | 10.5 |
| " | 6.6 | 7.6 | 8.0 |
| " | 8.0 | 8.5 | 8.0 |
| " | 7.1 | 7.4 | 7.9 |
| " | 8.0 | 8.2 | 8.4 |
| DMDPEDA/DBB | 7.0 | 7.1 | 7.4 |
| " | 8.2 | 6.5 | 7.0 |
| " | 7.6 | 6.5 | 8.5 |
| " | 8.5 | 7.5 | 8.1 |
| TAMBTACEDA/DBB | 7.7 | 6.5 | 7.8 |

EXAMPLE 10

Corrosion Inhibition

Corrosion inhibition properties for the functional ionene polymer compositions were determined by means of potentiostatic polarization. This method provides a simple and direct means of quantifying metallic corrosion by measuring the polarizing effect of an applied current on the natural equilibrium of the partial anodic and cathodic currents inherent in the oxidation/reduction reaction of corrosion, and the resulting displacement of the potential of a metal electrode which is undergoing such corrosion. The applied current is measured as a function of the potential of the corroding electrode, which is controlled by means of a potentiostat. In particular, the Tafel slope extrapolation procedure was employed to determine corrosion rates. The potential of the working (corroding) electrode was plotted against the logarithm of the applied current. The resulting curve was linear in the so-called Tafel region and this was extrapolated to the corrosion potential value, which is the potential at which the metal of the working electrode corrodes in an aerated aqueous environment. The intercept point corresponds to the corrosion rate of the system expressed in terms of current density. In order to convert this value to the more conventional expression of corrosion rate in terms of mils per year (mpy) or milligrams per square decimeter per day (mdd), the following conversion was used:

$$mpy = 0.46\ I\mu a/\text{cm}^2$$

$$mdd = 2.5\ I\mu a/\text{cm}^2$$

where $I\mu a/\text{cm}^2$ is the current density at the point of intercept expressed as milliamperes per square centimeter. This conversion is based on the relationship of the current density at the equilibrium or corrosion potential, and the amount of iron consumed by corrosion [expressed as milligram per square decimeter of surface per day (mdd) or as mils per year (mpy)] which may be derived through Faraday's Law. For example, a current density of $4.0 \times 10^{-7}$ amperes/cm$^2$ is equal to 1.0 mg/dm$^2$/day.

The tests were conducted in synthetic Pittsburgh water at an initial pH of 7.0, with a final pH as indicated in the table below. Steel electrodes were used in the polarization test cells and the corrosion inhibitor concentrations were calculated on the basis of active material. The results of the potentiostatic polarization tests are illustrated in the table of data below.

| Composition | Dosage ppm | Final pH | Corrosion Rate mdd |
|---|---|---|---|
| TPEDA | 100 | 7.7 | 61 |
| " | 500 | 7.6 | 69 |
| TPEDA/DBB | 100 | 7.6 | 59 |
| " | 500 | 7.3 | 65 |
| DMDPEDA | 100 | 7.8 | 59 |
| " | 500 | 7.6 | 110 |
| TAMBTACEDA | 100 | 7.7 | 71 |
| " | 500 | 7.8 | 71 |
| DMDPEDA/DBB | 100 | 7.6 | 81 |
| " | 500 | 7.3 | 90 |
| TAMBTACEDA/DBB | 100 | 7.6 | 50 |
| " | 500 | 7.5 | 66 |
| Control | — | — | 90-95 |

EXAMPLE 11

Flocculation

Flocculation properties for the functional ionene polymer compositions were determined by means of a visual flocculation dosage test. In accordance with the procedures of this test, test samples were prepared by dissolving 1 g. of each polymer to be evaluated in 1 l. of water. Next, the test medium, consisting of a suspension of silica, was prepared by dispersing 200 mg. of Ludox/HS, manufactured by DuPont de Nemours & Co., Wilmington, Delaware, in 1 l. of water. The suspension was determined to have a pH of 9.0. Overall, the test procedure involved the incremental addition of polymer solution samples to the test medium, while it was being stirred at 100 r.p.m., until floc formation occurred. The increments of polymer solution addition were initially 1 ml. (= 1 mg. of polymer) until the test medium became turbid. Increments were then reduced to 0.5 ml. until floc formation occurred. The total dosage of polymer in mg./l. of test medium required for flocculation was noted. The results of these evaluations are illustrated in the following table of values.

| Composition | Dosage (mg./l.) for Floc Formation |
|---|---|
| TAMBTACEDA/DBB | 10 |
| DMDPEDA/DBB | 75 |

What is claimed is:

1. A polymer composition represented by the formula:

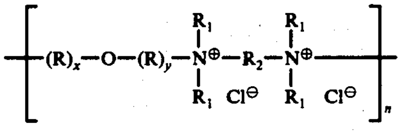

wherein R is $CH_2$ or substituted $CH_2$ groups where one of the hydrogen atoms of the group is replaced by alkyl or hydroxymethyl;

wherein $R_1$ represents the group:

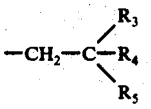

where $R_3$ is hydrogen, lower alkyl of from 1 to 4 carbon atoms, or lower alkenyl of from 1 to 4 carbon atoms;

where $R_4$ is hydrogen, halogen, straight or branched alkyl, cycloalkyl, aryl, alkaryl, or aralkyl; and where $R_5$ is a member selected from the group consisting of:

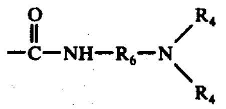

and

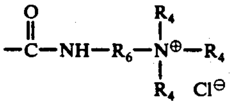

where $R_4$ has the same meaning as above;

where $R_6$ is selected from the group consisting of straight or branched alkyl, cycloalkyl, hydroxyalkyl and alkoxyalkyl;

wherein $R_2$ is a straight or branched alkyl chain of 1 to 18 carbon atoms, which may be interrupted by one or more atoms of oxygen or sulfur; aralkyl or cycloalkyl;

wherein *x* and *y* are integers from 1 to 10; and *n* is an integer of 2 or greater.

2. A polymer composition having recurring units represented by the formula:

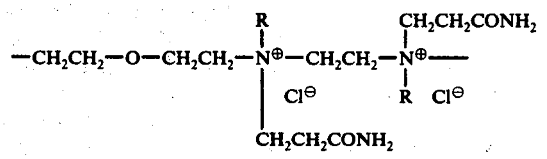

wherein R is $CH_3$ or $CH_2CH_2CONH_2$.

3. A polymer composition having recurring units represented by the formula:

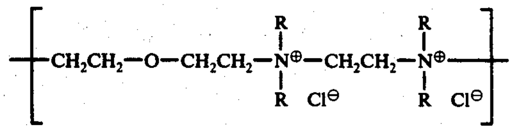

wherein R is

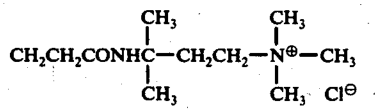

* * * * *

UNITED STATES PATENT AND TRADEMARK OFFICE

CERTIFICATE OF CORRECTION

PATENT NO. : 4,075,136

DATED : February 21, 1978

INVENTOR(S) : Raymond Joseph Schaper

It is certified that error appears in the above-identified patent and that said Letters Patent are hereby corrected as shown below:

Column 1, line 32: "components" should read --compounds--.

Column 4, line 43: "$R^-$" should read --$A^-$--.

Column 8, Column 9, Column 11 and Colum 13: Column headings for chart should be titled as follows:

| R' | R''' | Generic Group Formula for R'' | Name and Structure of Resulting Functional Group |
|---|---|---|---|

Column 11, second set of formulae: Under the column titled "Generic Group Formula for R''" should be the following formula:

$$-\overset{O}{\overset{\|}{C}}-O-R'''-SO_3^-M^+$$

UNITED STATES PATENT AND TRADEMARK OFFICE

CERTIFICATE OF CORRECTION

PATENT NO. : 4,075,136

DATED : February 21, 1978

INVENTOR(S) : Raymond Joseph Schaper

It is certified that error appears in the above-identified patent and that said Letters Patent are hereby corrected as shown below:

Column 11, second set of formulae: Under the column titled "Name and Structure of Resulting Functional Group" should be the following formula:

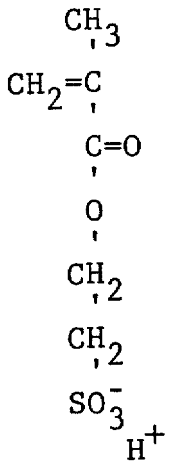

UNITED STATES PATENT AND TRADEMARK OFFICE

CERTIFICATE OF CORRECTION

PATENT NO. : 4,075,136

DATED : February 21, 1978

INVENTOR(S) : Raymond Joseph Schaper

It is certified that error appears in the above-identified patent and that said Letters Patent are hereby corrected as shown below:

Column 11, fourth set of formulae: Under the column titled "Name and Structure of Resulting Functional Group should be the formula:

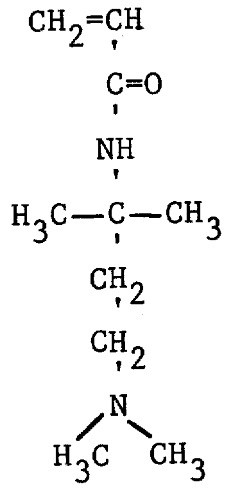

acrylamidomethylbutyl dimethyl amine

UNITED STATES PATENT OFFICE
CERTIFICATE OF CORRECTION

PATENT NO. : 4,075,136

DATED : February 21, 1978

INVENTOR(S) : Raymond Joseph Schaper

It is certified that error appears in the above-identified patent and that said Letters Patent are hereby corrected as shown below:

Column 13, first set of formulae: Under the column titled "R'" the following formula should be deleted:

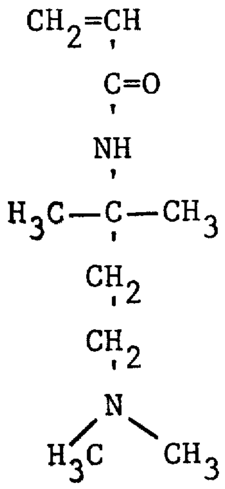

UNITED STATES PATENT AND TRADEMARK OFFICE
CERTIFICATE OF CORRECTION

PATENT NO. : 4,075,136

DATED : February 21, 1978

INVENTOR(S) : Raymond Joseph Schaper

It is certified that error appears in the above-identified patent and that said Letters Patent are hereby corrected as shown below:

Column 13, first set of formulae: Under the column titled "Name and Structure of Resulting Functional Group" "acrylamidomethylbutyl dimethyl amine" should be deleted.

Column 13, second set of formulae: Under the column titled "R'''" the structure should read as follows:

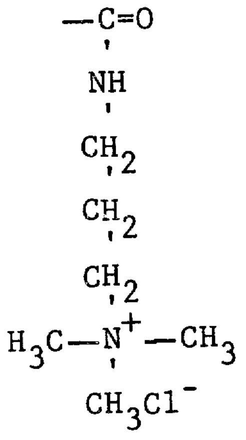

UNITED STATES PATENT AND TRADEMARK OFFICE

CERTIFICATE OF CORRECTION

PATENT NO. : 4,075,136 Page 6 of 6

DATED : February 21, 1978

INVENTOR(S) : Raymond Joseph Schaper

It is certified that error appears in the above-identified patent and that said Letters Patent are hereby corrected as shown below:

Column 13, fifth set of formulae: Under the column titled "Name and Structure of Rsulting Functional Group" the structure should read as follows:

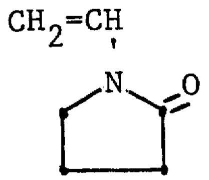

Column 15, line 52: "printink" should read --printing--.

Column 16, line 16: "aver" should read --over--.

Column 16, line 57: "N,N,N'" should be deleted.

Signed and Sealed this

*Ninth* Day of *December 1980*

[SEAL]

*Attest:*

SIDNEY A. DIAMOND

*Attesting Officer* *Commissioner of Patents and Trademarks*